(12) United States Patent
Deng et al.

(10) Patent No.: US 6,287,802 B1
(45) Date of Patent: Sep. 11, 2001

(54) EXT2 GENE

(75) Inventors: Han Xiang Deng; Chao Hong Fan, both of Chicago, IL (US); Jiahui Xia, Hunan (CN)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/915,337

(22) Filed: Aug. 21, 1997

(30) Foreign Application Priority Data

Oct. 21, 1996 (CN) ................................................ 96121928

(51) Int. Cl.[7] ............................ C12P 21/06; C12N 15/00; C12N 5/00
(52) U.S. Cl. ..................... 435/69.1; 435/320.1; 435/325; 536/23.2; 536/23.1; 536/23.5
(58) Field of Search .................................. 536/23.1, 23.5, 536/23.2; 530/350; 435/320.1, 69.1, 325

(56) References Cited

PUBLICATIONS

Database Genbank, Accession No. U72263, Jul. 1997.*
Database Genbank, Accession No. U62740, Sep. 1996.*
Database Genbank Accession No. U64511, Oct. 1996.*
Jung Ahn, et al.; Cloning of the putative tumour suppressor gene for hereditary multiple exostoses(EXT1); Nature Genetics, vol. 11, Oct. 1995, pp. 137–143.
Wim Wuyts, et al.; Refinement of the Multiple Extoses Locus (EXT2) to a 3–cM Interval on Chromosome 11; American Journal Human Genetics, 57, 1995, pp. 382–387.
Dominique Stickens, et al.; The EXT2 multiple exostoses gene defines a family of putative tumour suppressor genes; Nature Genetics, vol. 14, Sep. 1996, pp. 25–32.
Wim Wuyts, et al.; Positional cloning of a gene involved in hereditary multiple exostoses; Human Molecular Genetics, 1996, vol. 5, No. 10, pp. 1547–1557.

* cited by examiner

*Primary Examiner*—Yvonne Eyler
(74) *Attorney, Agent, or Firm*—William T. Han; Ratner & Prestia; William T. King

(57) ABSTRACT

EXT2 polypeptides and DNA(RNA) encoding such enzyme and a procedure for producing such polypeptides by recombinant techniques is disclosed. Also disclosed are methods for utilizing such EXT2 in the development of treatments for to hereditary multiple exotoses and cancers, such as chondrosarcoma, among others, are also disclosed. Also disclosed are diagnostic assays for detecting diseases related to mutations in the nucleic acid sequences and altered concentrations of the polypeptides.

10 Claims, 4 Drawing Sheets

1. EXT2 cDNA sequence and predicated amino acid sequence ctcgccagcccagactcggccctggcagtggcggctggcgattcggaccgatccgacctgggcggaggtggcccgcgc
ccgcggcatgagccggtgaccaagctcggggccgagcgggaggcagccgtggccgaggagtgtgaggaagaggctgt
ctgtgtcatt

| atg | tgt | gcg | tcg | gtc | aag | tat | aat | atc | cgg | ggt | cct | gcc | ctc | atc | cca | aga | atg | aag |
|-----|-----|-----|-----|-----|-----|-----|-----|-----|-----|-----|-----|-----|-----|-----|-----|-----|-----|-----|
| M | C | A | S | V | K | Y | N | I | R | G | P | A | L | I | P | R | M | K |

| acc | aag | cac | cga | atc | tac | tat | atc | acc | ctc | ttc | tcc | att | gtc | ctc | ctg | ggc | ctc | att |
|-----|-----|-----|-----|-----|-----|-----|-----|-----|-----|-----|-----|-----|-----|-----|-----|-----|-----|-----|
| T | K | H | R | I | Y | Y | I | T | L | F | S | I | V | L | L | G | L | I |

| gcc | act | ggc | atg | ttt | cag | ttt | tgg | ccc | cat | tct | atc | gag | tcc | tca | aat | gac | tgg | aat |
|-----|-----|-----|-----|-----|-----|-----|-----|-----|-----|-----|-----|-----|-----|-----|-----|-----|-----|-----|
| A | T | G | M | F | Q | F | W | P | H | S | I | E | S | S | N | D | W | N |

| gta | gag | aag | cgc | agc | atc | cgt | gat | gtg | ccg | gtt | gtt | agg | ctg | cca | gcc | gac | agt | ccc |
|-----|-----|-----|-----|-----|-----|-----|-----|-----|-----|-----|-----|-----|-----|-----|-----|-----|-----|-----|
| V | E | K | R | S | I | R | D | V | P | V | V | R | L | P | A | D | S | P |

| atc | cca | gag | cgg | ggg | gat | ctc | agt | tgc | aga | atg | cac | acg | tgt | ttt | gat | gtc | tat | cgc |
|-----|-----|-----|-----|-----|-----|-----|-----|-----|-----|-----|-----|-----|-----|-----|-----|-----|-----|-----|
| I | P | E | R | G | D | L | S | C | R | M | H | T | C | F | D | V | Y | R |

| tgt | ggc | ttc | aac | cca | aag | aac | aaa | atc | aag | gtg | tat | atc | tat | gct | ctg | aaa | aag | tac |
|-----|-----|-----|-----|-----|-----|-----|-----|-----|-----|-----|-----|-----|-----|-----|-----|-----|-----|-----|
| C | G | F | N | P | K | N | K | I | K | V | Y | I | Y | A | L | K | K | Y |

| gtg | gat | gac | ttt | ggc | gtc | tct | gtc | agc | aac | acc | atc | tcc | cgg | gag | tat | aat | gaa | ctg |
|-----|-----|-----|-----|-----|-----|-----|-----|-----|-----|-----|-----|-----|-----|-----|-----|-----|-----|-----|
| V | D | D | F | G | V | S | V | S | N | T | I | S | R | E | Y | N | E | L |

| ctc | atg | gcc | atc | tca | gac | agt | gac | tac | tac | act | gat | gac | atc | aac | cgg | gcc | tgt | ctg |
|-----|-----|-----|-----|-----|-----|-----|-----|-----|-----|-----|-----|-----|-----|-----|-----|-----|-----|-----|
| L | M | A | I | S | D | S | D | Y | Y | T | D | D | I | N | R | A | C | L |

| ttt | gtt | ccc | tcc | atc | gat | gtg | ctt | aac | cag | aac | aca | ctg | cgc | atc | aag | gag | aca | gca |
|-----|-----|-----|-----|-----|-----|-----|-----|-----|-----|-----|-----|-----|-----|-----|-----|-----|-----|-----|
| F | V | P | S | I | D | V | L | N | Q | N | T | L | R | I | K | E | T | A |

| caa | gcg | atg | gcc | cag | ctc | tct | agg | tgg | gat | cga | ggt | acg | aat | cac | ctg | ttg | ttc | aac |
|-----|-----|-----|-----|-----|-----|-----|-----|-----|-----|-----|-----|-----|-----|-----|-----|-----|-----|-----|
| Q | A | M | A | Q | L | S | R | W | D | R | G | T | N | H | L | L | F | N |

| atg | ttg | cct | gga | ggt | ccc | cca | gat | tat | aac | aca | gcc | ctg | gat | gtc | ccc | aga | gac | agg |
|-----|-----|-----|-----|-----|-----|-----|-----|-----|-----|-----|-----|-----|-----|-----|-----|-----|-----|-----|
| M | L | P | G | G | P | P | D | Y | N | T | A | L | D | V | P | R | D | R |

FIG. 1A

```
gcc ctg ttg gct ggt ggc ggc ttt tct acg tgg act tac cgg caa ggc tac gat gtc
 A   L   L   A   G   G   G   F   S   T   W   T   Y   R   Q   G   Y   D   V agc att cct gtc tat agt cca ctg tca gct gag gtg gat ctt cca gag aaa gga cca
 S   I   P   V   Y   S   P   L   S   A   E   V   D   L   P   E   K   G   P ggt cca cgg caa tac ttc ctc ctg tca tct cag gtg ggt ctc cat cct gag tac aga
 G   P   R   Q   Y   F   L   L   S   S   Q   V   G   L   H   P   E   Y   R gag gac cta gaa gcc ctc cag gtc aaa cat gga gag tca gtg tta gta ctc gat aaa
 E   D   L   E   A   L   Q   V   K   H   G   E   S   V   L   V   L   D   K tgc acc aac ctc tca gag ggt gtc ctt tct gtc cgt aag cgc tgc cac aag cac cag
 C   T   N   L   S   E   G   V   L   S   V   R   K   R   C   H   K   H   Q gtc ttc gat tac cca cag gtg cta cag gag gct act ttc tgt gtg gtt ctt cgt gga
 V   F   D   Y   P   Q   V   L   Q   E   A   T   F   C   V   V   L   R   G gct cgg ctg ggc cag gca gta ttg agc gat gtg tta caa gct ggc tgt gtc ccg gtt
 A   R   L   G   Q   A   V   L   S   D   V   L   Q   A   G   C   V   P   V gtc att gca gac tcc tat att ttg cct ttc tct gaa gtt ctt gac tgg aag aga gca
 V   I   A   D   S   Y   I   L   P   F   S   E   V   L   D   W   K   R   A tct gtg gtt gta cca gaa gaa aag atg tca gat gtg tac agt att ttg cag agc atc
 S   V   V   V   P   E   E   K   M   S   D   V   Y   S   I   L   Q   S   I ccc caa aga cag att gaa gaa atg cag aga cag ctc ttc atg gaa cca gtc agg aga
 P   Q   R   Q   I   E   E   M   Q   R   Q   L   F   M   E   P   V   R   R gag aac tgg tca gct gct aat cac caa atg aac tcc ctg atc tgg cct agg gaa cag
 E   N   W   S   A   A   N   H   Q   M   N   S   L   I   W   P   R   E   Q tgg gat tca cag att atc aat gac cgg atc tat cca tat gct gcc atc tcc tat gaa
 W   D   S   Q   I   I   N   D   R   I   Y   P   Y   A   A   I   S   Y   E gaa tgg aat gac cct cct gct gtg aag tgg ggc agc gtg agc aat cca ctc ttc ctc
 E   W   N   D   P   P   A   V   K   W   G   S   V   S   N   P   L   F   L ccg ctg atc cca cca cag tct caa ggg ttc acc gcc ata gtc ctc acc tac gac cga
 P   L   I   P   P   Q   S   Q   G   F   T   A   I   V   L   T   Y   D   R gta gag agc ctc ttc cgg gtc atc act gaa gtg tcc aag gtg ccc agt cta tcc aaa
```

FIG. 1B

```
    V   E   S   L   F   R   V   I   T   E   V   S   K   V   P   S   L   S   K
cta ctt gtc gtc tgg aat aat cag aat aaa aac cct cca gaa gat tct ctc tgg ccc
 L   L   V   V   W   N   N   Q   N   K   N   P   P   E   D   S   L   W   P aaa atc cgg gtt cca tta aaa gtt gtg agg act gct gaa aac aag tta agt aac cgt
 K   I   R   V   P   L   K   V   V   R   T   A   E   N   K   L   S   N   R ttc ttc cct tat gat gaa atc gag aca gaa gct gtt ctg gcc att gat gat gat atc
 F   F   P   Y   D   E   I   E   T   E   A   V   L   A   I   D   D   D   I att atg ctg acc tct gac gag ctg caa ttt ggt tat gag gtc tgg cgg gaa ttt cct
 I   M   L   T   S   D   E   L   Q   F   G   Y   E   V   W   R   E   F   P gac cgg ttg gtg ggt tac ccg gat cgt ctg cat ctc tgg gac cat gag atg aat aag
 D   R   L   V   G   Y   P   D   R   L   H   L   W   D   H   E   M   N   K tgg aag tat gag tct gag tgg acg aat gaa gtg tcc atg gtg ctc act ggg gca gct
 W   K   Y   E   S   E   W   T   N   E   V   S   M   V   L   T   G   A   A ttt tat cac aag tat ttt aat tac ctg tat acc tac aaa atg cct ggg gat atc aag
 F   Y   H   K   Y   F   N   Y   L   Y   T   Y   K   M   P   G   D   I   K aac tgg gta gat gct cat atg aac tgt gaa gat att gcc atg aac ttc ctg gtg gcc
 N   W   V   D   A   H   M   N   C   E   D   I   A   M   N   F   L   V   A aac gtc acg gga aaa gca gtt atc aag gta acc cca cga aag aaa ttc aag tgt cct
 N   V   T   G   K   A   V   I   K   V   T   P   R   K   K   F   K   C   P gag tgc aca gcc ata gat ggg ctt tca cta gac caa aca cac atg gtg gag agg tca
 E   C   T   A   I   D   G   L   S   L   D   Q   T   H   M   V   E   R   S gag tgc atc aac aag ttt gct tca gtc ttc ggg acc atg cct ctc aag gtg gtg gaa
 E   C   I   N   K   F   A   S   V   F   G   T   M   P   L   K   V   V   E cac cga gct gac cct gtc ctg tac aaa gat gac ttt cct gag aag ctg aag agc ttc
 H   R   A   D   P   V   L   Y   K   D   D   F   P   E   K   L   K   S   F ccc aac att ggc agc tta tga
 P   N   I   G   S   L   Stop
``` aacgtgtcattggtggaggtctgaatgtgaggctgggacagagggagagaacaaggcctcccagcactctgatgtcaga
gtagtaggttaagggtggaaggttgacctacttggatcttggcatgcacccacctaacccactttctcaagaacaagaac

FIG. 1C

```
ctagaatgaatatccaagcacctcgagctatgcaacctctgttcttgtatttcttatgatctctgatgggttcttctcgaa
aatgccaagtggaagactttgtgggcatgctcccagatttaaatccagctgaggctccctttgttttcagttccatgtaa
caatctggaaggaaacttcacggacaggaagactgctggagaagagaagcgtgttagcccatttgaggtctggggaatc
atgtaaagggtacccagacctcacttttagttatttacatcaatgagttctttcagggaaccaaacccagaattcggtgc
aaaagccaaacatcttggtgggatttgataaatgccttgggacctggagtgctgggcttgtgcacaggaagagcaccag
ccgctgagtcaggatcctgtcagttccatgagctattcctctttggtttggcttttgatatgattaaaattattttttatt
cctttaaaa
```

FIG. 1D

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3003 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
CTCGCCAGCC CAGACTCGGC CCTGGCAGTG GCGGCTGGCG ATTCGGACCG ATCCGACCTG     60
GGCGGAGGTG GCCCGCGCCC CGCGGCATGA GCCGGTGACC AAGCTCGGGG CCGAGCGGGA    120
GGCAGCCGTG GCCGAGGAGT GTGAGGAAGA GGCTGTCTGT GTCATTATGT GTGCGTCGGT    180
CAAGTATAAT ATCCGGGGTC CTGCCCTCAT CCCAAGAATG AAGACCAAGC ACCGAATCTA    240
CTATATCACC CTCTTCTCCA TTGTCCTCCT GGGCCTCATT GCCACTGGCA TGTTTCAGTT    300
TTGGCCCCAT TCTATCGAGT CCTCAAATGA CTGGAATGTA GAGAAGCGCA GCATCCGTGA    360
TGTGCCGGTT GTTAGGCTGC CAGCCGACAG TCCCATCCCA GAGCGGGGGG ATCTCAGTTG    420
CAGAATGCAC ACGTGTTTTG ATGTCTATCG CTGTGGCTTC AACCCAAAGA ACAAAATCAA    480
GGTGTATATC TATGCTCTGA AAAGTACGT GGATGACTTT GGCGTCTCTG TCAGCAACAC    540
CATCTCCCGG GAGTATAATG AACTGCTCAT GGCCATCTCA GACAGTGACT ACTACACTGA    600
TGACATCAAC CGGGCCTGTC TGTTTGTTCC CTCCATCGAT GTGCTTAACC AGAACACACT    660
GCGCATCAAG GAGACAGCAC AAGCGATGGC CCAGCTCTCT AGGTGGGATC GAGGTACGAA    720
TCACCTGTTG TTCAACATGT TGCCTGGAGG TCCCCCAGAT TATAACACAG CCCTGGATGT    780
CCCCAGAGAC AGGGCCCTGT TGGCTGGTGG CGGCTTTTCT ACGTGGACTT ACCGGCAAGG    840
CTACGATGTC AGCATTCCTG TCTATAGTCC ACTGTCAGCT GAGGTGGATC TTCCAGAGAA    900
AGGACCAGGT CCACGGCAAT ACTTCCTCCT GTCATCTCAG GTGGGTCTCC ATCCTGAGTA    960
CAGAGAGGAC CTAGAAGCCC TCCAGGTCAA ACATGGAGAG TCAGTGTTAG TACTCGATAA   1020
ATGCACCAAC CTCTCAGAGG GTGTCCTTTC TGTCCGTAAG CGCTGCCACA AGCACCAGGT   1080
CTTCGATTAC CCACAGGTGC TACAGGAGGC TACTTTCTGT GTGGTTCTTC GTGGAGCTCG   1140
GCTGGGCCAG GCAGTATTGA GCGATGTGTT ACAAGCTGGC TGTGTCCCGG TTGTCATTGC   1200
AGACTCCTAT ATTTTGCCTT TCTCTGAAGT TCTTGACTGG AAGAGAGCAT CTGTGGTTGT   1260
ACCAGAAGAA AAGATGTCAG ATGTGTACAG TATTTTGCAG AGCATCCCCC AAAGACAGAT   1320
TGAAGAAATG CAGAGACAGC TCTTCATGGA ACCAGTCAGG AGAGAGAACT GGTCAGCTGC   1380
TAATCACCAA ATGAACTCCC TGATCTGGCC TAGGGAACAG TGGGATTCAC AGATTATCAA   1440
TGACCGGATC TATCCATATG CTGCCATCTC CTATGAAGAA TGGAATGACC CTCCTGCTGT   1500
GAAGTGGGGC AGCGTGAGCA ATCCACTCTT CCTCCCGCTG ATCCCACCAC AGTCTCAAGG   1560
```

```
GTTCACCGCC ATAGTCCTCA CCTACGACCG AGTAGAGAGC CTCTTCCGGG TCATCACTGA  1620

AGTGTCCAAG GTGCCCAGTC TATCCAAACT ACTTGTCGTC TGGAATAATC AGAATAAAAA  1680

CCCTCCAGAA GATTCTCTCT GGCCCAAAAT CCGGGTTCCA TTAAAAGTTG TGAGGACTGC  1740

TGAAAACAAG TTAAGTAACC GTTTCTTCCC TTATGATGAA ATCGAGACAG AAGCTGTTCT  1800

GGCCATTGAT GATGATATCA TTATGCTGAC CTCTGACGAG CTGCAATTTG GTTATGAGGT  1860

CTGGCGGGAA TTTCCTGACC GGTTGGTGGG TTACCCGGAT CGTCTGCATC TCTGGGACCA  1920

TGAGATGAAT AAGTGGAAGT ATGAGTCTGA GTGGACGAAT GAAGTGTCCA TGGTGCTCAC  1980

TGGGGCAGCT TTTTATCACA AGTATTTTAA TTACCTGTAT ACCTACAAAA TGCCTGGGGA  2040

TATCAAGAAC TGGGTAGATG CTCATATGAA CTGTGAAGAT ATTGCCATGA ACTTCCTGGT  2100

GGCCAACGTC ACGGGAAAAG CAGTTATCAA GGTAACCCCA CGAAAGAAAT TCAAGTGTCC  2160

TGAGTGCACA GCCATAGATG GGCTTTCACT AGACCAAACA CACATGGTGG AGAGGTCAGA  2220

GTGCATCAAC AAGTTTGCTT CAGTCTTCGG GACCATGCCT CTCAAGGTGG TGGAACACCG  2280

AGCTGACCCT GTCCTGTACA AAGATGACTT TCCTGAGAAG CTGAAGAGCT TCCCCAACAT  2340

TGGCAGCTTA TGAAACGTGT CATTGGTGGA GGTCTGAATG TGAGGCTGGG ACAGAGGGAG  2400

AGAACAAGGC CTCCCAGCAC TCTGATGTCA GAGTAGTAGG TTAAGGGTGG AAGGTTGACC  2460

TACTTGGATC TTGGCATGCA CCCACCTAAC CCACTTTCTC AAGAACAAGA ACCTAGAATG  2520

AATATCCAAG CACCTCGAGC TATGCAACCT CTGTTCTTGT ATTTCTTATG ATCTCTGATG  2580

GGTTCTTCTC GAAAATGCCA AGTGGAAGAC TTTGTGGGCA TGCTCCCAGA TTTAAATCCA  2640

GCTGAGGCTC CCTTTGTTTT CAGTTCCATG TAACAATCTG GAAGGAAACT TCACGGACAG  2700

GAAGACTGCT GGAGAAGAGA AGCGTGTTAG CCCATTTGAG GTCTGGGGAA TCATGTAAAG  2760

GGTACCCAGA CCTCACTTTT AGTTATTTAC ATCAATGAGT TCTTTCAGGG AACCAAACCC  2820

AGAATTCGGT GCAAAAGCCA AACATCTTGG TGGGATTTGA TAAATGCCTT GGGACCTGGA  2880

GTGCTGGGCT TGTGCACAGG AAGAGCACCA GCCGCTGAGT CAGGATCCTG TCAGTTCCAT  2940

GAGCTATTCC TCTTTGGTTT GGCTTTTTGA TATGATTAAA ATTATTTTTT ATTCCTTTTA  3000

AAA                                                                3003
```

(2) INFORMATION FOR SEQ ID NO:2:

(i) SEQUENCE CHARACTERISTICS:
        (A) LENGTH: 728 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Met Cys Ala Ser Val Lys Tyr Asn Ile Arg Gly Pro Ala Leu Ile Pro
 1               5                  10                  15

Arg Met Lys Thr Lys His Arg Ile Tyr Tyr Ile Thr Leu Phe Ser Ile
            20                  25                  30
```

```
Val Leu Leu Gly Leu Ile Ala Thr Gly Met Phe Gln Phe Trp Pro His
        35                  40                  45
Ser Ile Glu Ser Ser Asn Asp Trp Asn Val Glu Lys Arg Ser Ile Arg
     50                  55                  60
Asp Val Pro Val Val Arg Leu Pro Ala Asp Ser Pro Ile Pro Glu Arg
 65                  70                  75                  80
Gly Asp Leu Ser Cys Arg Met His Thr Cys Phe Asp Val Tyr Arg Cys
                 85                  90                  95
Gly Phe Asn Pro Lys Asn Lys Ile Lys Val Tyr Ile Tyr Ala Leu Lys
                100                 105                 110
Lys Tyr Val Asp Asp Phe Gly Val Ser Val Ser Asn Thr Ile Ser Arg
        115                 120                 125
Glu Tyr Asn Glu Leu Leu Met Ala Ile Ser Asp Ser Asp Tyr Tyr Thr
        130                 135                 140
Asp Asp Ile Asn Arg Ala Cys Leu Phe Val Pro Ser Ile Asp Val Leu
145                 150                 155                 160
Asn Gln Asn Thr Leu Arg Ile Lys Glu Thr Ala Gln Ala Met Ala Gln
                165                 170                 175
Leu Ser Arg Trp Asp Arg Gly Thr Asn His Leu Leu Phe Asn Met Leu
                180                 185                 190
Pro Gly Gly Pro Pro Asp Tyr Asn Thr Ala Leu Asp Val Pro Arg Asp
            195                 200                 205
Arg Ala Leu Leu Ala Gly Gly Phe Ser Thr Trp Thr Tyr Arg Gln
        210                 215                 220
Gly Tyr Asp Val Ser Ile Pro Val Tyr Ser Pro Leu Ser Ala Glu Val
225                 230                 235                 240
Asp Leu Pro Glu Lys Gly Pro Gly Pro Arg Gln Tyr Phe Leu Leu Ser
                245                 250                 255
Ser Gln Val Gly Leu His Pro Glu Tyr Arg Glu Asp Leu Glu Ala Leu
                260                 265                 270
Gln Val Lys His Gly Glu Ser Val Leu Val Leu Asp Lys Cys Thr Asn
        275                 280                 285
Leu Ser Glu Gly Val Leu Ser Val Arg Lys Arg Cys His Lys His Gln
        290                 295                 300
Val Phe Asp Tyr Pro Gln Val Leu Gln Glu Ala Thr Phe Cys Val Val
305                 310                 315                 320
Leu Arg Gly Ala Arg Leu Gly Gln Ala Val Leu Ser Asp Val Leu Gln
                325                 330                 335
Ala Gly Cys Val Pro Val Val Ile Ala Asp Ser Tyr Ile Leu Pro Phe
                340                 345                 350
Ser Glu Val Leu Asp Trp Lys Arg Ala Ser Val Val Val Pro Glu Glu
        355                 360                 365
Lys Met Ser Asp Val Tyr Ser Ile Leu Gln Ser Ile Pro Gln Arg Gln
    370                 375                 380
Ile Glu Glu Met Gln Arg Gln Leu Phe Met Glu Pro Val Arg Arg Glu
385                 390                 395                 400
Asn Trp Ser Ala Ala Asn His Gln Met Asn Ser Leu Ile Trp Pro Arg
                405                 410                 415
Glu Gln Trp Asp Ser Gln Ile Ile Asn Asp Arg Ile Tyr Pro Tyr Ala
            420                 425                 430
Ala Ile Ser Tyr Glu Glu Trp Asn Asp Pro Pro Ala Val Lys Trp Gly
        435                 440                 445
```

```
Ser Val Ser Asn Pro Leu Phe Leu Pro Leu Ile Pro Pro Gln Ser Gln
    450                 455                 460

Gly Phe Thr Ala Ile Val Leu Thr Tyr Asp Arg Val Glu Ser Leu Phe
465                     470                 475                 480

Arg Val Ile Thr Glu Val Ser Lys Val Pro Ser Leu Ser Lys Leu Leu
                485                 490                 495

Val Val Trp Asn Asn Gln Asn Lys Asn Pro Pro Glu Asp Ser Leu Trp
            500                 505                 510

Pro Lys Ile Arg Val Pro Leu Lys Val Val Arg Thr Ala Glu Asn Lys
        515                 520                 525

Leu Ser Asn Arg Phe Phe Pro Tyr Asp Glu Ile Glu Thr Glu Ala Val
    530                 535                 540

Leu Ala Ile Asp Asp Asp Ile Ile Met Leu Thr Ser Asp Glu Leu Gln
545                 550                 555                 560

Phe Gly Tyr Glu Val Trp Arg Glu Phe Pro Asp Arg Leu Val Gly Tyr
                565                 570                 575

Pro Asp Arg Leu His Leu Trp Asp His Glu Met Asn Lys Trp Lys Tyr
            580                 585                 590

Glu Ser Glu Trp Thr Asn Glu Val Ser Met Val Leu Thr Gly Ala Ala
        595                 600                 605

Phe Tyr His Lys Tyr Phe Asn Tyr Leu Tyr Thr Tyr Lys Met Pro Gly
    610                 615                 620

Asp Ile Lys Asn Trp Val Asp Ala His Met Asn Cys Glu Asp Ile Ala
625                 630                 635                 640

Met Asn Phe Leu Val Ala Asn Val Thr Gly Lys Ala Val Ile Lys Val
                645                 650                 655

Thr Pro Arg Lys Lys Phe Lys Cys Pro Glu Cys Thr Ala Ile Asp Gly
            660                 665                 670

Leu Ser Leu Asp Gln Thr His Met Val Glu Arg Ser Glu Cys Ile Asn
        675                 680                 685

Lys Phe Ala Ser Val Phe Gly Thr Met Pro Leu Lys Val Val Glu His
    690                 695                 700

Arg Ala Asp Pro Val Leu Tyr Lys Asp Asp Phe Pro Glu Lys Leu Lys
705                 710                 715                 720

Ser Phe Pro Asn Ile Gly Ser Leu
                725
```

EXT2 GENE

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to novel polynucleotides and polypeptides of the family of hereditary multiple exostoses, hereinafter referred to as EXT2.

BACKGROUND OF THE INVENTION

Hereditary multiple exostoses (HME or EXT) is an autosomal dominant disorder characterized by multiple exostoses most commonly arising from the juxtaepiphyseal region of the long bones. Other bones that can be involved include the pectoral and pelvic girdles, rib, and less frequently, vertebrae, sternum, skull, and carpal and tarsal bones. In addition, abnormal bone modeling, particularly of the long ones, is a feature. This causes bowing, shortness, cortical irregularities, and metaphyseal widening of the involved bones, leading to the deformities of the forearms and disproportionate short stature in severe cases. The exostoses can give rise to complications such as compression or irritation of adjacent nerves, vessels, and tendons, and urinary or intestinal obstruction. The most serious complication is sarcomatous degeneration, which occurs in 0.5 to 2% of affected individuals (Hennekam, R. C. M., Hereditary Multiple Exostoses, *J. Med. Genet.* 28:262–266, (1991)). Hecht et al. (Hecht, J. T.; Hogue, D.; Strong, L. C.; Hansen, M. F.; Blanton, S. H.; Wagner, M., Hereditary Multiple Exostosis and Chondrosarcoma: Linkage to Chromosome 11 and Loss of Heterozygosity for EXT–Linked Markers on Chromosomes 11 and 8., *Am. J Hum. Genet.* 56:1125–1131 (1995)) reported that a prevalence of chondrosarcoma in multiple exostoses of 2% to 5% compared with age-adjusted incidence rate of 1/100,000 for all bone cancers. Multiple exostoses are part of the Langer-Giedion syndrome (150230), which appears to be a contiguous gene syndrome, due to deletion in the 8q24 region.

Genetic linkage studies established three loci for multiple exostosis genes. They are located at chromosome 8, 11 and 19, respectively.

Cook et al. (Cook, A.; Raskind, W.; Blanton, S. H.; Pauli, R. M.; Gregg, R. G.; Francomano, C. A.; Puffenberger, E.; Conrad, E. U.; Schmale, G.; Schellenberg, G.; Wijsman, E.; Hecht, J. T.; Wells, D.; Wagner, M. J., Genetic Heterogeneity in Families with Hereditary Multiple Exostoses., *Am. J Hun. Genet.* 53:71–79 (1993)) concluded that about 70% of multiple exostoses families show linkage to markers in the 8q24. 11–q24.13 region. Investigating 2 large exostoses pedigrees in which linkage to markers from 8q24 was excluded, Wu et al. (Wu, Y.-Q.; Heutink, P.; de Vries, B. B. A.; Sandkuijl, L. A.; van den Ouweland, A. M. W.; Niermeijer, M. F.; Galjaard. H.; Reyniers, E.; Willems, P. J.; Halley, D. J. J., Assignment of a Second Locus for Multiple Exostoses to the Pericentromeric Region of Chromosome 11, *Hum. Molec. Genet.* 3:167–171 (1994)) found evidence of linkage to microsatellite markers from the proximal short and long arms of chromosome 11. The highest lod score by 2-point analysis was found with D11S554; maximum lod= 7.148 at theta=0.03.

Hecht et al. (1995) and Raskind et al. (Raskind, W. H.; Conrad, E. U.; Chansky, H.; Matsushita, M., Loss of Heterozygosity in Chondrosarcomas for Markers Linked to Hereditary Multiple Exostoses Loci on Chromosomes 8 and 11, *Am. J Hum. Genet.* 56:1132–1139 (1995)) presented evidence suggesting that the EXT1 gene on chromosome 8 and the EXT2 gene on chromosome 11 have tumor-suppressor function. They found loss of heterozygosity for markers linked to these 2 genes in chondrosarcomas originating in individuals with multiple exostoses and in sporadic chondrosarcomas.

As part of a larger study to determine the frequency of the 3 EXT types in the United States, Hecht et al. (1995) ascertained a large multigenerational family with multiple exostosis and in 1 member a chondrosarcoma. This family demonstrated linkage of the disease to chromosome 11 markers. Constitutional and tumor DNAs from the affected family member were compared using short-tandem-repeat (STR) markers from chromosomes 8, 11, and 19. Loss of heterozygosity (LOH) in the tumor was observed for chromosome 8 and 11 markers, but chromosome 19 markers were intact. Hecht et al. (1995) observed an apparent deletion of D11S903 in constitutional DNA from all affected individuals and in the tumor sample. These results indicated that EXT2 gene maps to the region containing D11S903, which is flanked by D11S1355 and D11S1361. The authors similarly analyzed additional constitutional and chondrosarcoma DNA from 6 unrelated individuals, 2 of whom had EXT. One tumor from an individual with EXT demonstrated LOH for chromosome 8 markers, and a person with a sporadic chondrosarcoma was found to have a tumor-specific LOH and a homozygous deletion of chromosome 11 markers. These findings suggested to Hecht et al. (1995) that EXT genes may be tumor-suppressor genes and that the initiation of tumor development may follow a multistep model. Raskind et al. (1995) found loss of constitutional heterozygosity at polymorphic loci linked to genes involved in the multiple exostoses. They detected LOH for markers linked to EXT1 on chromosome 8 in a chondrosarcoma that arose in a man with multiple exostoses. They also found LOH for markers linked to EXT1 in 4 of 17 sporadic chondrosarcomas, and 7 showed LOH for markers linked to EXT2. In all, Raskind et al. (1995) observed LOH for markers linked to EXT 1 or EXT2 in 44% of the 18 tumors, whereas heterozygosity was retained for markers on 19p linked to EXT3. These findings also suggested a tumor suppressor role for EXT genes.

Studying 7 extended multiple exostoses families, all linked to the EXT2 locus, Wuyts et al. (Wuyts, W.; Ramlakhan, S.; Van Hul, W.; Hecht, J. T.; van den Ouweland, A. M. W.; Raskind, W. H.; Hofstede, F. C. Reyniers, E.; Wells, D. E.; de Vries, B.; Conrad, E. U.; Hill, A.; Zalatayev, D.; Weissenbach, J.; Wagner, M. J.; Bakker, E.; Halley, D. J. J.; Willems, P. J., Refinement of the Multiple Exostoses Locus (EXT2) to a 3-cM Interval on Chromosome 11, *Am J. Hum. Genet.* 57: 382–387 (1995)) refined the localization of the EXT2 gene to a 3-cM region flanked by D11S1355 and D11S1361/D11S554. The findings indicated that the EXT2 gene is located on 11p12-p11. The refined localization excluded a number of putative candidate genes located in the pericentromeric region of chromosome 11.

Support for the localization of the EXT2 gene was provided also by the report of McGaughran et al. (McGaughran, J. M.; Ward, H. B.; Evans, D. G. R., WAGR Syndrome and Multiple Exostoses in a Patient with Del(11)(p11.2p14.2), *J. Med. Genet.* 32: 823–824, (1995)), who described a patient with the combination of multiple exostoses with the WAGR syndrome (Wilms tumor, aniridia, genital anomalies, and mental retardation; 194070), a well documented contiguous gene syndrome resulting from deletion of 11p13. Their patient showed adel(11) (p14.2p11.2).

As pointed out by Potocki et al. (Potocki, L.; Greenberg, F.; Shaffer, L. G., Interstitial Deletion of 11(p12p11.2): A Rare Chromosomal Syndrome with Mental Retardation, Parietal Foramina, and Multiple exostoses. (Abstract), *Am. J Hum. Genet.* 57: A123 (1995)) the description of the contiguous gene syndrome resulting from interstitial deletion of 11p, del(11)(p12p11.2), including multiple exostoses as a feature, provided confirmation of the mapping of EXT2. Other features of this contiguous gene syndrome are mental retardation and parietal foramina, known as Catlin marks. Potocki and Shaffer (Potocki, L.; Shaffer, L. G., Interstitial Deletion of 11(p11.2p12): a Newly Described Contiguous Gene Deletion Syndrome Involving the Gene for Hereditary Multiple Exostoses (EXT2), *Am. J Med. Genet.* 62:319–325 (1996)) reported the clinical and molecular findings in a further patient with an 11(p12p11.2) deletion. Cytogenetic and molecular analysis demonstrated a de novo, paternally-derived deletion for markers known to be tightly linked to EXT2. The patient had an unusual facies (bilateral epicanthal folds, ptosis, short philtrum, and downturned upper lip), mental retardation, multiple exostoses, brachycephaly, and bilateral parietal foramina Ahn et al. (Ahn, J. et al., Cloning of the Putative Tumor Suppressor Gene for Hereditary Multiple Exostoses, *Nature Genet.,* 11, 137–143 (1995)) cloned and characterized a cDNA that spans chromosomal breakpoints previously identified in 2 multiple exostoses patients. Furthermore, the gene harbored frameshift mutations in affected members of 2 EXT1 families. The cDNA had a coding region of 2,238bp with no apparent homology to other known gene sequences.

Stickens et al. (Stickens, D.; Clines, G.; Burbee, D.; Ramos, P.; Thomas, S.; Hogue, D.; Hecht, J. T.; Lovett, M.; Evans, G. A., The EXT2 Multiple Exostoses Gene Defines a Family of Putative Tumour Suppressor Genes, *Nature Genet.* 14:25–32 (1996)) reported the identification and characterization of the EXT2 gene on chromosome 11. The EXT2 gene contains 7 exons and encodes a 718-amino acid polypeptide. By Northern analysis, they detected a 3.5-kb transcript in almost all tissues. Alternative splicing generates a mninor 3.7-kb transcript in some tissues. The gene shows striking sequence similarity to the EXT1 gene on chromosome 8. Multigenerational family with chromosome 11-linked multiple exostoses described by Hecht et al. (1995) in which one family member developed a malignant chondrosarcoma. In this family, an apparent deletion of the region including polymorphic marker D11S903 was observed in all affected members. In tumor tissue derived from the patient with chondrosarcoma, Stickens et al. (1996) observed that polymorphic marker D11S903 was deleted and that there was LOH for other chromosome 11 markers. In the initial study of the EXT2 candidate gene for mutations, they performed SSCP analysis using DNA from affected members of 3 unrelated families. In 1 of 2 alleles of 1 patient, deletion of nucleotides 784 to 787 was identified, resulting in a frameshift and a premature termination of the EXT2 gene product.

Using genoric DNA library constructed from 11p11–12 by microdissection, several cDNA clones from human placenta cDNA library were isolated. One of these clones shares 59% homology with EXT1 cDNA in some parts. This gene was further mapped by fluorescence in situ hybridization to chromosome 11p11, which is the exact region where EXT2 gene is located. By cDNA library screening and 5'RACE techniques, the full cDNA sequence was cloned. It is predicted that this cDNA encodes 728 amino acids. Both cDNA and amino acids sequence share striking similarities with EXT1. Thus, this gene is responsible for chromosome 11 linked multiple exostosis.

By comparing the cDNA sequence of the present invention with the reported EXT2 gene sequence, they are 90bp difference in the middle of the coding region which results in 30 amino acids difference from the reported one by Stickens (Stickens, 1996).

Stickens et al isolated this cDNA from brain cDNA library, while the present cDNA is from placenta cDNA library. The difference between our DNA sequence and theirs indicates that there are at least two isoforms of EXT2-encoded proteins.

This indicates that EXT2 genes are useful as therapeutic targets. Clearly there is a need for identification and characterization of further genes which can play a role in preventing, ameliorating or correcting dysfunctions or diseases, including, but not limited to, hereditary multiple exotoses and cancers, such as chondrosarcoma, among others.

SUMMARY OF THE INVENTION

Toward these ends, and others, it is an object of the present invention to provide polypeptides, inter alia, that have been identified as novel EXT2 by homology between the amino acid sequence set out in FIGS. 1A–1D and known amino acid sequences of other proteins such as EXT1.

It is a further object of the invention, moreover, to provide polynucleotides that encode EXT2, particularly polynucleotides that encode the polypeptide herein designated by SEQ ID NO:2.

In a particularly preferred embodiment of this aspect of the invention, the polynucleotide comprises the region encoding EXT2 in the sequence set out in FIGS. 1A–1D.

In accordance with this aspect of the invention, there are provided isolated nucleic acid molecules encoding EXT2, including mnRNAs, cDNAs, genomic DNAs and fragments and, in further embodiments of this aspect of the invention, biologically, diagnostically, clinically or therapeutically useful variants, analogs or derivatives thereof, including fragments of the variants, analogs and derivatives.

Among the particularly preferred embodiments of this aspect of the invention are naturally occurring allelic variants of EXT2.

It also is an object of the invention to provide particularly EXT2 polypeptides, that may be employed for therapeutic purposes, for example, in the treatment of hereditary multiple exotoses and cancers, such as chondrosarcoma, among others.

In accordance with this aspect of the invention, there are provided novel polypeptides of human origin, referred to herein as EXT2, as well as biologically, diagnostically or therapeutically useful fragments, variants and derivatives thereof, variants and derivatives of the fragments, and analogs of the foregoing.

Among the particularly preferred embodiments of this aspect of the invention are variants of EXT2 encoded by naturally occurring alleles of the EXT2 gene.

In accordance with another aspect of the present invention, there are provided methods of screening for compounds which bind to and activate or inhibit activation of the polypeptide of the present invention.

It is another object of the invention to provide a process for producing the aforementioned polypeptides, polypeptide fragments, variants and derivatives, fragments of the variants and derivatives, and analogs of the foregoing. In a preferred embodiment of this aspect of the invention, there are provided methods for producing the aforementioned EXT2 polypeptides comprising culturing host cells having expressibly incorporated therein an exogenously-derived EXT2-encoding polynucleotide under conditions for expression of EXT2 in the host, expressing the EXT2 in the host cells, and then recovering the expressed polypeptide from the host cells.

In accordance with another object of the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing EXT2 expression in cells by determining EXT2 polypeptides or EXT2-encoding mRNA; to treat hereditary multiple exotoses and cancers, such as chondrosarcoma, among others, in vitro, ex vivo or in vivo by exposing cells to EXT2 polypeptides or polynucleotides as disclosed herein; assaying genetic variation and aberrations, such as defects, in EXT2 genes; and administering a EXT2 polypeptide or polynucleotide to an organism to augment EXT2 function or remediate EXT2 dysfunction.

In accordance with still another embodiment of the present invention, there is provided a process of using such activating compounds to stimulate polypeptide of the present invention for the treatment of conditions related to the under-expression of EXT2.

In accordance with another aspect of the present invention, there is provided a process of using such inhibiting compounds for treating conditions associated with over-expression of the EXT2.

In accordance with yet another aspect of the present invention, there is provided non-naturally occurring synthetic, isolated and/or recombinant EXT2 polypeptides which are fragments, consensus fragments and/or sequences having conservative amino acid substitutions of at least one domain of the EXT2 of the present invention, such polypeptide being capable of modulating, quantitatively or qualitatively, EXT2 binding to its receptor or ligands.

In accordance with still another aspect of the present invention, there are provided synthetic or recombinant EXT2 polypeptides, conservative substitution and derivatives thereof, antibodies thereto, anti-idiotype antibodies, compositions and methods that can be useful as potential modulators of EXT2 function, by binding to the polypeptides or modulating polypeptide binding, due to their expected biological properties, which may be used in diagnostic, therapeutic and/or research applications.

It is still another object of the present invention to provide synthetic, isolated or recombinant polypeptides which are designed to inhibit or mimic various EXT2 or fragments thereof.

In accordance with certain preferred embodiments of this and other aspects of the invention, there are provided probes that hybridize to EXT2 sequences.

In certain additional preferred embodiments of this aspect of the invention, there are provided antibodies against EXT2 polypeptides. In certain particularly preferred embodiments in this regard, the antibodies are highly selective for EXT2.

In accordance with another aspect of the present invention, there are provided EXT2 agonists. Among preferred agonists are molecules that mimic the EXT2 polypeptide, that bind to EXT2-binding molecules or receptors, and that elicit or augment EXT2-induced responses. Also among preferred agonists are molecules that interact with EXT2 or EXT2 polypeptides, or with other modulators of EXT2 activities, thereby potentiating or augmenting an effect of EXT2 or more than one effect of EXT 2.

In accordance with yet another aspect of the present invention, there are provided EXT2 antagonists. Among preferred antagonists are those which mimic the EXT2 polypeptide so as to bind to EXT2 receptors or binding molecules but not elicit a EXT2-induced response or more than one EXT2-induced response. Also among preferred antagonists are molecules that bind to or interact with EXT2 so as to inhibit an effect of EXT2 or more than one effect of EXT2 or to prevent expression of EXT2.

In a further aspect of the invention, there are provided compositions comprising a EXT2 polynucleotide or a EXT2 polypeptide for administration to cells in vitro, to cells ex vivo and to cells in vivo, or to a multicellular organism. In certain particularly preferred embodiments of this aspect of the invention, the compositions comprise a EXT2 polynucleotide for expression of a EXT2 polypeptide in a host organism for treatment of disease. Particularly preferred in this regard is expression in a hereditary multiple exotoses and cancer, such as chondrosarcoma, patient for treatment of a dysfunction associated with aberrant endogenous activity of EXT2.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A–1D shows the nucleotide sequence and deduced amino acid sequence of EXT2 (SEQ ID NOS: 1 and 2).

GLOSSARY

The following illustrative explanations are provided to facilitate understanding of certain terms used frequently herein, particularly in the examples. The explanations are provided as a convenience and are not meant to limit the invention. "Digestion" of DNA refers to catalytic cleavage of a DNA with an enzyme such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylaride gel, using well known methods that are routine for those skilled in the art. "Genetic element" generally means a polynucleotide comprising a region that encodes a polypeptide or a region that regulates replication, transcription, translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others. "Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as Sambrook et al.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5'phosphate of another polynucleotide, such as another oligonucleotide. As is well known, this reaction can be prevented selectively, where desired, by removing the 5'phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case "p" preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill may readily construct any number of other plasmids suitable for use in the invention. The properties, construction and use of such plasmids, as well as other vectors, in the present invention will be readily apparent to those of skill from the present disclosure. "Polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide, as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide also includes DNAs or RNAs as described above that contain one or more modified bases. Thus, DNAs or RNAs with backbones modified for stability or for other reasons are polynucleotides, as that term is intended herein. Moreover, DNAs or RNAs comprising unusual bases, such as inosine, or modified bases, such as tritylated bases, to name just two examples, are polynucleotides, as the term is used herein. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art. Known modifications which may be present in polypeptides of the present invention include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications including glycosylation, lipid attachment, sulfation, gamma-carboxylation of glutamic acid residues, hydroxylation and ADP-ribosylation are described in most basic texts such as PROTEINS—STRUCTURE AND MOLECULAR PROPERTIES, 2nd Ed., T. E. Creighton, W. H. Freeman and Company, New York, 1993. Detailed reviews are also available on this subject. See e.g., Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth. Enzymol.*, 1990, 182:626–646 and Rattan et al., "Protein Synthesis: Posttranslational Modifications and Aging", *Ann. N.Y. Acad Sci.*, 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttransiational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

Variants include polynucleotides that differ in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. As also noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. EP-A-O 464 533 (Canadian counterpart 2045869) discloses fusion proteins comprising various portions of constant region of immunoglobin molecules together with another human protein or part thereof. In many cases, employing an inmmunoglobulin Fc region as a part of a fusion protein is advantageous for use in therapy and diagnosis resulting in, for example, improved pharmacokinetic properties (EP-A 0232 262). On the other hand, for some uses it would be desirable to be able to delete the Fc part after the fusion protein has been expressed, detected and purified. Accordingly, it may be desirable to link the components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as, shIL5-α have been fused with Fc portions for use in high-throughput screening assays to identify antagonists of hIL-5. See, D. Bennett et al., *Journal of Molecular Recognition*, 1995, 8:52–58; and K. Johanson et al., *The Journal of Biological Chemistry*, 1995, 270(16):9459–9471.

Thus, this invention also relates to genetically engineered soluble fusion proteins comprised of EXT2, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In one embodiment, the Fc part can be removed simple by incorporation of a cleavage sequence which can be cleaved with blood clotting factor Xa. This invention further relates to processes for the preparation of these fusion proteins by genetic engineering, and to the use thereof for diagnosis and therapy. Yet a further aspect of the invention relates to polynucleotides encoding such fusion proteins.

Membrane bound proteins are particularly useful in the formation of fusion proteins. Such proteins are generally characterized as possessing three distinct structural regions, an extracellular domain, a transmembrane domain, and a cytoplasmic domain. This invention contemplates the use of one or more of these regions as components of a fusion protein. Examples of such fusion protein technology can be found in WO94/29458 and WO94/22914.

"Binding molecules" (or otherwise called "interaction molecules" or "receptor component factors") refer to molecules, including receptors, that specifically bind to or interact with polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity", which means the degree of sequence relatedness between two polypeptide or two polynucleotide sequences as determined by the identity of the match between two strings of such sequences. Both identity and similarity can be readily calculated (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A.M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). There exist a number of methods to measure identity and similarity between two polynucleotide or polypeptide sequences, and the terms "identity" and "similarity" are well known to skilled artisans (Carillo, H., and Lipton, D., SIAM *J. Applied Math.*, 1988, 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J. Applied Math.*, 1988, 48:1073. Preferred methods to determine identity are designed to give the largest match between the two sequences tested. Methods to determine identity and similarity are also codified in computer programs. Preferred computer program methods to determine identity and similarity between two sequences include, but are not limited to, GCG program package (Devereux, J., et al., *Nucleic Acids Research*, 1984, 12(1):387), BLAST, FASTA (Atschul, S. F. et al., *J. Molec. Biol.*, 1990, 215:403).

DESCRIPTION OF THE INVENTION

The present invention relates to novel EXT2 polypeptides and polynucleotides, among other things, as described in greater detail below. In particular, the invention relates to polypeptides and polynucleotides of a novel EXT2, which is related by amino acid sequence homology to EXT2. The invention relates especially to EXT2 having the nucleotide and amino acid sequences set out in FIGS. 1A–1D.

Polynucleotides

In accordance with one aspect of the present invention, there are provided isolated polynucleotides which encode the EXT2 polypeptide having the deduced amino acid sequence of FIGS. 1A–1D.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A–1D, SEQ ID NO: 1. It also may be a polynucleotide with a different sequence, which, as a result of the redundancy (degeneracy) of the genetic code, also encodes the polypeptide of FIGS. 1A–1D, SEQ ID NO: 2.

Polynucleotides of the present invention which encode the polypeptide of FIGS. 1A–1D may include, but are not limited to, the coding sequence for the mature polypeptide, by itself; the coding sequence for the mature polypeptide and additional coding sequences; and the coding sequence of the mature polypeptide, with or without the aforementioned additional coding sequences, together with additional, non-coding sequences. Examples of additional coding sequence include, but are not limited to, sequences encoding a leader or secretory sequence, such as a pre-, or pro- or prepro-protein sequence. Examples of additional non-coding sequences include, but are not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexahistidine peptide, such as that provided in the pQE vector (Qiagen, Inc.). As described in Gentz et al., *Proc. Natl. Acad. Sci., USA,* 1989, 86:821–824, for instance, hexahistidine provides for convenient purification of the fusion protein. In other embodiments the marker sequence is HA tag. The HA tag corresponds to an epitope derived of influenza hemagglutinin protein, which has been described by Wilson et al., Cell, 1984, 37:767, for instance. Many other such tags are commercially available.

In accordance with the foregoing, the term "polynucleotide encoding a polypeptide" as used herein encompasses polynucleotides which include, by virtue of the redundancy of the genetic code, any sequence encoding a polypeptide of the present invention, particularly the EXT2 having the amino acid sequence set out in FIGS. 1A–1D, SEQ ID NO:2. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1A–1D. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of EXT2 set out in FIGS. 1A–1D; variants, analogs, derivatives and fragments thereof, and fragments of the variants, analogs and derivatives.

Further particularly preferred in this regard are polynucleotides encoding EXT2 variants, analogs, derivatives and fragments, and variants, analogs and derivatives of the fragments, which have the amino acid sequence of the EXT2 polypeptide of FIGS. 1A–1D in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the EXT2. Also especially preferred in this regard are conservative substitutions. Most highly preferred are polynucleotides encoding polypeptides having the amino acid sequence of FIGS. 1A–1D, without substitutions.

Further preferred embodiments of the invention are polynucleotides that are at least 96% identical to a polynucleotide encoding the EXT2 polypeptide having the amino acid sequence set out in FIGS. 1A–1D, and polynucleotides which are complementary to such polynucleotides Particularly preferred embodiments in this respect, moreover, are polynucleotides which encode polypeptides which retain substantially the same biological function or activity as the mature polypeptide encoded by the cDNA of FIGS. 1A–1D.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 96% identity between the sequences.

As discussed additionally herein regarding polynucleotide assays of the invention, for instance, polynucleotides of the invention as discussed above, may be used as hybridization probes for cDNA and genomic DNA, to isolate full-length cDNAs and genomic clones encoding EXT2 and to isolate cDNA and genomic clones of other genes that have a high sequence similarity to the EXT2 gene. Such probes generally will comprise at least 15 nucleotides. Preferably, such probes will have at least 30 nucleotides and may have at least 50 nucleotides. Particularly preferred probes will range between 30 and 50 nucleotides.

For example, the coding region of the EXT2 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine the members of the library to which the probe hybridizes to.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to a EXT2 polypeptide which has the deduced amino acid sequence of FIGS. 1A–1D, SEQ ID NO: 2.

The invention also relates to fragments, analogs and derivatives of these polypeptides. The terms "fragment," "derivative" and "analog" when referring to the polypeptide of FIGS. 1A–1D, mean a polypeptide which retains essentially the same biological function or activity as such polypeptide, i.e. functions as EXT2, or retains the ability to bind any receptors or binding molecules even though the polypeptide does not function as the EXT2 polypeptide. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A–1D may be: (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of EXT2 set out in FIGS. 1A–1D as SEQ ID NO:2, variants, analogs, derivatives and fragments thereof, and variants, analogs and derivatives of the fragments. Further particularly preferred embodiments of the invention in this regard are polypeptides having the amino acid sequence of EXT2, variants, analogs, derivatives and fragments thereof, and variants, analogs and derivatives of the fragments which retain the activity/function of this polypeptide.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the EXT2 polypeptide of FIGS. 1A–1D, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the polypeptide. Also especially preferred in this regard are conservative substitutions. Most highly preferred are polypeptides having the amino acid sequence of FIGS. 1A–1D, SEQ ID NO:2, without substitutions.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 96% similarity (more preferably at least 96% identity) to the polypeptide of SEQ ID NO:2.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a EXT2 polypeptide of the present invention comprised within a precursor polypeptide designed for expression in a host and having heterologous pre- and pro-polypeptide regions fused to the amino terminus of the EXT2 fragment and an additional region fused to the carboxyl terminus of the fragment. Therefore, fragments in one aspect of the meaning intended herein, refers to the portion or portions of a fusion polypeptide or fusion protein derived from EXT2.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which contain polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al which is merely illustrative of the many laboratory manuals that detail these techniques.

In accordance with this aspect of the invention the vector may be, for example, a plasmid vector, a single- or double-stranded phage vector, or a single- or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced to express a protein by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct MRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate, as well as engender, expression. Generally, in accordance with many commonly practiced procedures, such regions will operate by controlling transcription. Examples include repressor binding sites and enhancers, among others.

Vectors for propagation and expression generally will include selectable markers. Selectable marker genes provide a phenotypic trait for selection of transformed host cells.

Preferred markers include, but are not limited to, dihydrofolate reductase or neomycin resistance for eukaryotic cell culture, and tetracycline or ampicillin resistance genes for culturing E. coli and other bacteria. Such markers may also be suitable for amplification. Alternatively, the vectors may contain additional markers for this purpose.

The vector containing a selected polynucleotide sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmnid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp 1 gene of S. cerevisiae.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment,. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terminus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium.* Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include the C127, 3T3, CHO, HeLa, human kidney 293 and BHK cell lines. and the COS-7 line of monkey kidney fibroblasts, described by Gluzman et al., Cell, 1981, 23:175.

Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

The EXT2 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be empconformation when the polypeconformation when the polypeptide is denatured during isolation and or purification.

Polypeptides of the present invention include naturally purified polypeptides, polypeptides produced by chemical synthetic procedures, and polypeptides produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

EXT2 polynucleotides and polypeptides may be used in accordance with the present invention for a variety of applications, particularly those that make use of the chemical and biological properties of the enzyme. Additional applications relate to diagnosis and to treatment of disorders of cells, tissues and organisms. These aspects of the invention are illustrated further by the following discussion.

Polynucleotide Assays

This invention is also related to the use of EXT2 polynucleotides to detect complementary polynucleotides for use, for example, as a diagnostic reagent. Detection of a mutated form of EXT2 associated with a dysfunction will provide a diagnostic tool that can add to or define diagnosis of a disease or susceptibility to a disease which results from under-expression, over-expression or altered expression of EXT2. Individuals carrying mutations in the EXT2 gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using PCR prior to analysis. PCR (Saiki et al., Nature, 1986, 324:163–166). RNA or cDNA may also be used in similar fashion. As an example, PCR primers complementary to the nucleic acid encoding EXT2 can be used to identify and analyze EXT2 expression and mutations. For example, deletions and insertions can be detected by a change in size of the amplified product in comparison to the normal genotype. Point mutations can be identified by hybridizing amplified DNA to radiolabeled EXT2 RNA or, radiolabeled EXT2 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 1985, 230:1242).

Sequence changes at specific locations may also be revealed by nuclease protection assays, such as RNase and S 1 protection or the chemical cleavage method (e.g., Cotton etal., *Proc. Natl. Acad. Sci., USA,* 1985, 85: 4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In accordance with a further aspect of the invention, there is provided a process for diagnosing or determining a susceptibility to hereditary multiple exotoses and cancers, such as chondrosarcoma, among others. A mutation in the EXT2 gene may be indicative of a susceptibility to hereditary multiple exotoses and cancers, such as chondrosarcoma, among others; and the nucleic acid sequences described above may be employed in an assay for ascertaining such susceptibility. Thus, for example, the assay may be employed to determine a mutation in a EXT2 gene, as herein described, such as a subtstitution, deletion, truncation, insertion, frame shift, etc., with such mutation being indicative of a susceptibility to hereditary multiple exotoses and cancers, such as chondrosarcoma, among others.

The invention provides a process for diagnosing diseases, particularly, hereditary multiple exotoses and cancers, such as chondrosarcoma, among others; comprising determining from a sample derived from a patient an abnormally decreased or increased level of expression of polynucleotide having the sequence of FIGS. 1A–1D, SEQ ID NO: 1. Decreased or increased expression of polynucleotide can be measured using any of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Polypeptide Assays

The present invention also relates to diagnostic assays for detecting levels of EXT2 protein in cells and tissues. Such assays may be quantitative or qualitative, Thus, for instance, a diagnostic assay in accordance with the invention for detecting under-expression of EXT2 protein compared to normal control tissue samples may be used to detect the presence of hereditary multiple exotoses and cancers, such as chondrosarcoma, among others. Assay techniques that can be used to determine levels of a protein, such as a EXT2 protein of the present invention, in a sample derived from a host are well-known to those of skill in the art. Such assay methods include radioimmunoassays, competitive-binding assays, Western Blot analysis and enzyme linked immunosorbent assays (ELISAs). Among these, ELISAs are frequently preferred. An ELISA assay initially comprises preparing an antibody specific to EXT2, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. The monoclonal antibody is then incubated in the dish during which time the monoclonal antibodies attach to any EXT2 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to EXT2 protein. Unattached reporter antibody is then washed out. Reagents for peroxidase activity, including a calorimetric substrate are then added to the dish. Immobilizperoperoxidase, linked to EXT2 through the primary and colored reaction product. The amount of color developed in a given time period indicates the amount of EXT2 protein present in the sample. Quantitative results typically are obtained by reference to a standard curve.

A competition assay may also be employed wherein antibodies specific to EXT2 attached to a solid support and labeled EXT2 and a sample derived from the host are passed over the solid support. The amount of detected label attached to the solid support can be correlated to a quantity of EXT2 in the sample.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against polypeptides corresponding to a sequence of the present invention can be obtained by various means well known to those of skill in the art. For example, in one embodiment, the polypeptide is directly injected into an animal, preferably a nonhuman. The antibody so obtained will then bind the polypeptide itself. In this embodiment, even a sequence encoding only a fragment of the polypeptide can be used to generate antibodies binding the whole native polypeptide. Such antibodies can then be used to isolate the polypeptide from tissues expressing that polypeptide.

For preparation of monoclonal antibodies, any technique which provides antibodies produced by continuous cell line cultures can be used. Examples include the hybridoma technique (Kohler, G. and Milstein, C., *Nature,* 1975, 256:495–497), the trioma technique, the human B-cell hybridoma technique (Kozbor et al., *Immunology Today,* 1983, 4:72) and the EBV-hybridoma technique (Cole et al., MONOCLONAL ANTIBODIES AND CANCER THERAPY, pg. 77–96, Alan R. Liss, Inc., 1985).

Techniques described for the production of single chain antibodies (U.S. Pat. No. 4,946,778) can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or to purify the polypeptide of the present invention by attachment of the antibody to a solid support for isolation and/or purification by affinity chromatography.

Antibodies against EXT2 may also be employed to inhibit hereditary multiple exotoses and cancers, such as chondrosarcoma, among others.

EXT2 Binding Molecules and Assays

EXT2 can also be used to isolate proteins which interact with it; this interaction can be a target for interference. Inhibitors of protein-protein interactions between EXT2 and other factors could lead to the development of pharmaceutical agents for the modulation of EXT2 activity.

Thus, this invention also provides a method for identification of binding molecules to EXT2. Genes encoding proteins for binding molecules to EXT2 can be identified by numerous methods known to those of skill in the art, for example, ligand panning and FACS sorting. Such methods are described in many laboratory manuals such as, for instance, Coligan et al., CURRENT PROTOCOLS IN IMMUNOLOGY 1, Chapter 5, 1991.

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, EXT2 cDNA is fused to a Gal4 transcription factor DNA binding domain and expressed in yeast cells. cDNA library members obtained from cells of interest are fused to a transactivation domain of Gal4. cDNA clones which express proteins which can interact with EXT2 will lead to reconstitution of Gal4 activity and transactivation of expression of a reporter gene such as Gal4-lacZ.

An alternative method involves screening of λgt11, λZAP (Stratagene) or equivalent cDNA expression libraries with recombinant EXT2. Recombinant EXT2 protein or fragments thereof are fused to small peptide tags such as FLAG, HSV or GST. The peptide tags can possess convenient phosphorylation sites for a kinase such as heart muscle creatine Ikinase or they can be biotinylated. Recombinant EXT2 can be phosphorylated with $^{32}[P]$ or used unlabeled and detected with streptavidin or antibodies against the tags. λgt11cDNA expression libraries are made from cells of interest and are incubated with the recombinant EXT2, washed and cDNA clones which interact with EXT2 isolated. Such methods are routinely used by skilled artisans. See, e.g., Sambrook et al.

Another method is the screening of a mammalian expression library. In this method, cDNAs are cloned into a vector between a mammalian promoter and polyadenylation site and transiently transfected in COS or 293 cells. Forty-eight hours later, the binding protein is detected by incubation of fixed and washed cells with labeled EXT2. In a preferred embodiment, the EXT2 is iodinated, and any bound EXT2 is detected by autoradiography. See Sims et al., *Science,* 1988, 241:585–589 and McMahan et al., *EMBO J.,* 1991, 10:2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing EXT2 bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA,* 1987, 84:3365 and Aruffo et al., *EMBO J.,* 1987, 6:3313. If the binding protein is secreted, its cDNA can be obtained by a similar pooling strategy once a binding or neutralizing assay has been established for assaying supernatants from transiently transfected cells. General methods for screening supernatants are disclosed in Wong et al., *Science,* 1985, 228:810–815.

Another method involves isolation of proteins interacting with EXT2 directly from cells. Fusion proteins of EXT2 with GST or small peptide tags are made and immobilized on beads. Biosynthetically labeled or unlabeled protein extracts from the cells of interest are prepared, incubated with the beads and washed with buffer. Proteins interacting with EXT2 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another method is immunoaffinity purification. Recombinant EXT2 is incubated with labeled or unlabeled cell extracts and immunoprecipitated with anti-human antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method involves screening of peptide libraries for binding partners. Recombinant tagged or labeled EXT2 is used to select peptides from a peptide or phosphopeptide library which interact with EXT2. Sequencing of the peptides leads to identification of consensus peptide sequences which might be found in interacting proteins.

Agonists and Antagonists—Assays and Molecules

The EXT2 of the present invention may be employed in a screening process for compounds which activate (agonists) or inhibit activation (antagonists) of this polypeptide.

For example, a cellular compartment, such as a membrane or a preparation thereof, such as a membrane-preparation, may be prepared from a cell that expresses a molecule that binds EXT2, such as a molecule of a signaling or regulatory pathway modulated by EXT2. The preparation is incubated with labeled EXT2 in the absence or presence of a candidate molecule which may be a EXT2 agonist or antagonist. The ability of the candidate molecule to bind the binding molecule is reflected in a decrease binding of the labeled ligand. Molecules which bind gratuitously, i.e., without inducing the effects of EXT2 on binding the EXT2 binding molecule, are most likely good antagonists. Molecules that bind well and elicit effects that are the same as or closely related to EXT2 are agonists.

EXT2-like effects of potential agonists and antagonists may be measured, for instance, by determining activity of a second messenger system following interaction of the candidate molecule with a cell or appropriate cell preparation, comparing the effect with that of EXT2 or molecules that elicit the same effects as EXT2. Second messanger systems that may be useful in this regard include are, but not limited to, cAMP guanylate cyclase, ion channel or phosphoinositide hydrolysis second messenger systems.

Another example of an assay for EXT2 antagonists is a competitive assay that combines EXT2 and a potential antagonist with membrane-bound EXT2 receptor molecules or recombinant EXT2 receptor molecules under appropriate conditions for a competitive inhibition assay. EXT2 can be labeled, such as by radioactivity, such that the number of EXT2 molecules bound to a receptor molecule can be determined accurately to assess the effectiveness of the potential antagonist.

Examples of potential antagonists include antibodies or, in some cases, oligonucleotides which bind to the polypeptide but do not elicit a second messenger response such that the activity of the polypeptide is prevented.

Potential antagonists also include proteins which are closely related to EXT2, i.e. a fragment of the polypeptide, which have lost enzymatic activity.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix —see Lee et aL, *Nucl. Acids Res.,* 1979, 6:3073; Cooney et al., *Science,* 1988, 241:456; and Dervan et al., *Science,* 1991, 251:1360), thereby preventing transcription and production of the EXT2. The antisense RNA oligonucleotide hybridizes to the mRNA in vivo and blocks translation of the mRNA molecule into the enzyme (antisense —see Okano, *J. Neurochem.,* (1991) 56:560; Oligodeoxynucleotides as Antisense Inhibitors of Gene Expression, CRC Press, Boca Raton, Fla. (1988)). The oligonucleotides described above can also be delivered to cells such that the antisense RNA or DNA is expressed in vivo to inhibit production of EXT2.

Another potential antagonist is a small molecule which binds to the polypeptide, making it inaccessible to binding molecules such that normal biological activity is prevented. Examples of small molecules include, but are not limited to, small peptides or peptide-like molecules.

Potential antagonists also include soluble forms of EXT2 e.g., fragments of the polypeptide, which bind to binding molecules, thus preventing the binding molecules from interacting with membrane bound EXT2.

The EXT2's are ubiquitous in the mammalian host and are responsible for many biological functions, including many pathologies. Accordingly, it is desirous to find compounds and drugs which stimulate enzyme activity on the one hand and which can inhibit the function of EXT2 on the other hand.

Antagonists for EXT2 may be employed for a variety of therapeutic and prophylactic purposes for such hereditary multiple exotoses and cancers, such as chondrosarcoma, among others.

This invention additionally provides a method of treating an abnormal condition related to an excess of EXT2 activity which comprises administering to a subject an inhibitor compound (antagonist) as hereinabove described along with a pharmaceutically acceptable carrier in an amount effective to inhibit activation of the enzyme, or by inhibiting a second signal, and thereby alleviating the abnormal condition.

In general, agonists for EXT2 are employed for therapeutic and prophylactic purposes for hereditary multiple exotoses and cancers, such as chondrosarcoma, among others.

The invention also provides a method of treating abnormal conditions related to an under-expression of EXT2 and its activity, which comprises administering to a subject a therapeutically effective amount of a compound which activates (agonist) the polypeptide, to thereby alleviate the abnormal conditions of hereditary multiple exotoses and cancers, such as chondrosarcoma, among others.

Compositions and Kits

The soluble form of EXT2, and compounds which activate or inhibit such enzyme, may be employed in combination with a suitable pharmaceutical carrier. Such compositions comprise a therapeutically effective amount of the polypeptide or compound, and a pharmaceutically acceptable carrier or excipient. Such carriers include, but are not limited to, saline, buffered saline, dextrose, water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, the administered dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

EXT2 polynucleotides, polypeptides, agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques,* 1989, 7:980–990. Cellular promoters such as eukaryotic cellular promoters including, but not limited to, the histone, RNA polymerase im, and β-actin promoters can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT- 19-17-H2, YCRE, YCRIP, GP+E-86, GP+envAm12, and DAN cell lines as described in Miller, A., *Human Gene Therapy,* 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLE

Gene Therapeutic Expression of EXT2

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted - the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

EXT2 cDNA capable of expressing active EXT2, is isolated. The ends of the fragment are modified, if necessary, for cloning into the vector. For instance, 5' overhanging may be treated with DNA polymerase to create blunt ends. 3' overhanging ends may be removed using SI nuclease. Linkers may be ligated to blunt ends with T4 DNA ligase.

Equal quantities of the Moloney murine leukemia virus linear backbone and the EXT2 fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the EXT2 gene is introduced into the packaging cells by standard techniques. Infectious viral particles containing the EXT2 gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce EXT2 product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated polynucleotide comprising a nucleotide sequence that encodes the amino acid sequence set forth in SEQ ID NO:2.

2. The polynucleotide of claim 1 wherein the polynucleotide is cDNA.

3. The polynucleotide of claim 1 wherein the polynucleotide is RNA.

4. An isolated polynucleotide comprising the nucleotide sequence set forth in SEQ ID NO: 1.

5. An isolated polynucleotide which encodes a polypeptide comprising the amino acid sequence set forth in SEQ ID NO.: 2.

6. An expression system comprising an isolated cDNA molecule, wherein said expression system produces a polypeptide comprising the amino acid sequence set forth in SEQ ID NO:2, when said expression system is present in a compatible host cell.

7. An isolated host cell comprising the vector of claim 6.

8. A process for producing a polypeptide comprising culturing a host cell of claim 7 under conditions sufficient for the production of said polypeptide and recovering said polypeptide from the culture.

9. A process for producing a cell which expresses a polypeptide comprising transforming or transfecting a host cell with the vector of claim 6 such that the cell, under appropriate culture conditions, expresses the polypeptide encoded by the cDNA contained in the vector.

10. A polynucleotide which is fully complementary over its entire length to the polynucleotide in any one of claims 4, 5, or 1.

* * * * *